Figure 1:
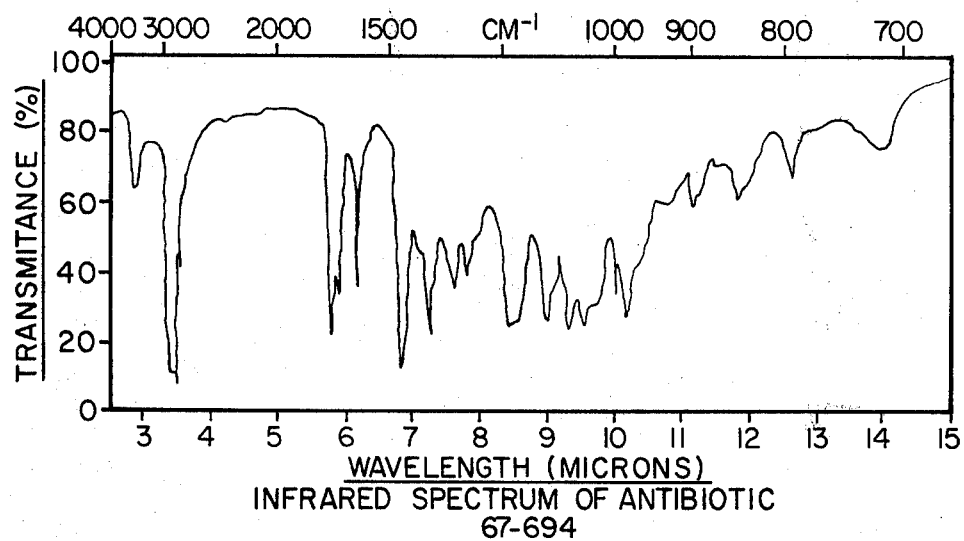

United States Patent [19]

Weinstein et al.

[11] 4,161,523

[45] Jul. 17, 1979

[54] ROSAMICIN ESTERS, ACID ADDITION SALTS AND METHODS FOR PRODUCTION THEREOF

[75] Inventors: Marvin J. Weinstein; Gerald H. Wagman, both of East Brunswick; Joseph A. Marquez, Montclair, all of N.J.

[73] Assignee: Schering Corporation, Kenilworth, N.J.

[21] Appl. No.: 516,338

[22] Filed: Oct. 21, 1974

Related U.S. Application Data

[63] Continuation-in-part of Ser. No. 303,883, Nov. 15, 1972, abandoned, which is a continuation-in-part of Ser. No. 4,916, Jan. 22, 1970, abandoned.

[51] Int. Cl.² ............................................. A61K 31/71
[52] U.S. Cl. ................................ 424/181; 536/17 R
[58] Field of Search ........................... 536/17; 424/181

[56] References Cited

U.S. PATENT DOCUMENTS 3,769,273  10/1973  Massey ........................ 260/210 AB

OTHER PUBLICATIONS

Weinstin, et al., Chemical Abstracts, vol. 75, 1971, p. 97266(a).

*Primary Examiner*—Jerome D. Goldberg
*Attorney, Agent, or Firm*—Raymond A. McDonald

[57] ABSTRACT

Antibiotic 67-694, (also known as rosamicin) a new broad spectrum antibiotic is described together with methods for its production via the cultivation under controlled conditions of *Micromonospora rosaria*, a new species of Micromonospora, and to methods for purifying and using the same. Its 2'-monoesters and its 3,2'-diesters and their acid addition salts also possess antibiotic activity.

21 Claims, 2 Drawing Figures

INFRARED SPECTRUM OF ANTIBIOTIC
67-694

NUCLEAR MAGNETIC RESONANCE SPECTRUM
OF ANTIBIOTIC
67-694

ROSAMICIN ESTERS, ACID ADDITION SALTS AND METHODS FOR PRODUCTION THEREOF

This application is a continuation-in-part of our co-pending application Ser. No. 303,883, filed Nov. 15, 1972 (now abandoned) which in turn is a continuation-in-part of application Ser. No. 4,916, filed Jan. 22, 1970 (now abandoned).

This invention relates to a novel composition of matter and to a process for the production thereof. More particularly, this invention relates to a new compound, hereinafter most often called Antibiotic 67-694, but sometimes referred to as rosamicin, to its non-toxic pharmaceutically acceptable 2'-monoesters and 3,2'-diesters and to the non-toxic pharmaceutically acceptable acid addition salts of each. This invention also relates to a process for the production of said antibiotic by microbiological fermentation of an elaborating microorganism.

Rosamicin is a biosynthetic elaborate obtained by cultivating a rosamicin producing species of Micromonospora in an aqueous nutrient medium. The antibiotic is a basic substance. It and its 2'-monoesters, its 3,2'-diesters and the acid addition salts of each, have the property of adversely affecting the growth of microorganisms, and in particular gram-positive bacteria.

The Microorganism

The microorganism used according to this invention for the production of Antibiotic 67-694 has been named *Micromonospora rosaria* (sometimes hereinafter referred to as *M. rosaria*). This species was isolated from a soil sample taken from a park (Little Thicket) in San Jacinto County, Texas. One of its strain characteristics is its ability to produce Antibiotic 67-694. A culture of the living organism has been made a part of the permanent collection of the Northern Utilization and Research Division, Agricultural Research Service, U.S. Department of Agriculture, Peoria, Illinois, where it has been assigned accession Number NRRL 3718. Sub-cultures of *M. rosaria* NRRL 3718 are readily available to the public from the foregoing Agency upon request. *M. rosaria* is aerobic and grows well on a variety of solid and liquid nutrient media. It exhibits especially good growth and antibiotic production under submerged aerobic conditions.

*M. rosaria* may be distinguished from other species of Micromonospora by a variety of taxonomical parameters. For example, after 14 days of incubation at 24°-26° C. on an agar medium comprising 3% NZ Amine Type A (Sheffield Chemical Company, Norwich, New York), 1% dextrose and 1.5% agar, growth is observed to be fair. Macroscopically, there is no apparent aerial mycelium. Colonies are slightly raised and are granular to weakly folded. No diffusible pigment is observed. In describing the color formations for this observation and others, the following system and references are employed: The color designations consist of two designators. The first is a color name taken from the "Descriptive Color Name Dictionary" by Taylor, Knoche and Granville published by the Container Corporation of America (1950) USA, with a color chip number corresponding to the color name, the chip number being taken from "The Color Harmony Manual", 4th Edition, 1958 published by The Container Corporation of America. The second designator consists of a color name and number which refers to the synonym or near synonym found in the National Bureau of Standards, Circular 553, November 1, 1955 (USA).

When grown on the above-mentioned medium the colony surface color is chestnut brown g4ni; moderate brown 58. Although colony surface color and pigment formation on a particular medium are generally characteristic of microorganisms both may be temporarily or permanently sub-cultured. Microscopically the mycelium is branched averaging 10 to 20μ in length. The mycelium has a diameter of approximately 0.6μ. Numerous chlamydospores are produced, the spores being up to 2.0μ in diameter. Conidia are not observed when the above-described medium is employed.

*M. rosaria* grows well at 27°-37° C.; no growth occurs at 50° C. A growing colony of *M. rosaria* will hydrolyze gelatin, milk and starch but will not reduce nitrate to nitrite. The foregoing tests are applied as described by Gordon, et al. J. Bacteriology 69:147 (1956) and 73:15 (1957).

Additional culture characteristics of *M. rosaria* are set forth in Table 1:

TABLE I

| Medium | Growth Characteristics |
|---|---|
| Bennett's Agar | Growth good, wine red diffusible pigment; plicate surface color g5pn, dark brown; dark brown 59 - to black. |
| Emerson's Agar | Growth fair, flat to furrowed, wine red diffusible pigment; surface color M6pn, dark brown mahogany; brownish gray 64 - to black |
| Tomato Paste Oatmeal Agar | Growth fair, plicate, no diffusible pigment surface color g4pn, dark brown; dark brown 59 |
| Glucose Asparagine Agar | No growth |
| Glucose Yeast Extract Agar | Growth good, plicate, wine red diffusible pigment |

*M. rosaria* is capable of utilizing a variety of carbon and nitrogen sources. In Table II there is set forth observations on carbohydrate utilization. A visual estimate of the degree of growth is observed in a medium consisting of 0.5% yeast extract, 1% of the indicated carbohydrate and 1.5% agar all in distilled water.

TABLE II
CARBOHYDRATE UTILIZATION

| Carbohydrate in Medium | Growth Characteristics |
|---|---|
| Arabinose | ++ black, flat, dark red diffusible pigment |
| Glucose | +++ furrowed, dark brown, wine red diffusible pigment |
| Galactose | + flat, brown, wine red diffusible pigment |
| Lactose | + brown, faint reddish diffusible pigment |
| Levulose | ++ flat to granular, dark brown, wine red diffusible pigment |
| Ribose | ++ dark, brown, flat, wine red diffusible pigment |
| Melibiose | ± |
| Melizitose | ± faint pinkish diffusible pigment |
| Rhamnose | ++ dark brown, flat, dark wine red diffusible pigment |
| Starch | ++ brown, no diffusible pigment |
| Sucrose | +++ black, granular, dark wine red diffusible pigment |
| Xylose | ++ brown, granular, wine red diffusible pigment |
| Mannitol | ++ dark brown, flat, dark red diffusible pigment |
| Growth on media containing, as its sole carbohydrate source, such compounds as glycerol, raffinose, inositol and dulcitol, is erratic; but is generally poor. | |
| Control 0.5% yeast | ± |

TABLE II-continued
CARBOHYDRATE UTILIZATION

| Carbohydrate in Medium | Growth Characteristics |
|---|---|
| extract | |

+ = fair
++ = good
+++ = very good
± = poor
− = very poor

In Table III, nitrogen utilization is set forth as determined by visual estimate of growth on agar plates in a medium consisting of 1% glucose, 1.5% agar, and the specific nitrogen source in the amount indicated, all in distilled water.

TABLE III
NITROGEN UTILIZATION

| Nitrogen Source | Growth Characteristics |
|---|---|
| 0.5% Difco Yeast Extract | Growth good, wine red diffusible pigment produced |
| 1.0% NZ Amine Type A | Growth good, no diffusible pigment produced |
| 1% Asparagine | Growth poor, faint pinkish diffusible pigment produced |
| 1% Glutamic Acid | Growth poor, pinkish diffusible pigment produced |
| 1% Sodium Nitrate | Growth poor, faint pinkish diffusible pigment produced |
| 1% Ammonium Nitrate | Growth poor, no diffusible pigment produced |

*Micromonospora rosaria* grows well and elaborates an antimicrobial product when grown on a number of nutrient media. Exemplary of such media are the following:

| Medium A | |
|---|---|
| Beef extract | 3 gms. |
| Tryptose | 5 gms. |
| Yeast extract | 5 gms. |
| Dextrose | 1 gm. |
| Potato starch | 24 gms. |
| Calcium carbonate | 2 gms. |
| Tap water | 1000 ml. |
| Medium B | |
| Yeast extract | 5 gms. |
| Corn steep solids | 1 gm. |
| Starch | 30 gms. |
| Calcium carbonate | 1 gm. |
| Tap water | 1000 ml. |
| Medium C | |
| Yeast extract | 7 gms. |
| Fish solubles | 1 gm. |
| Corn steep liquor solids | 1 gm. |
| Potato starch | 30 gms. |
| Tap water | 1000 ml. |

In addition, many other media may be utilized for the growth of *M. rosaria* and for the production of Antibiotic 67-694, those set forth above being only exemplary and in no way limiting.

PRODUCTION OF THE ANTIBIOTIC

Antibiotic 67-694, (rosamicin) is produced when the elaborating microorganism, *M. rosaria* is grown in an aqueous nutrient medium under submerged aerobic conditions. For small amounts of antibiotic, e.g. microgram to milligram quantities, surface culture in bottles or shake flasks may be employed. Typically, the nutrient medium is liquid, contains a carbon source such as an assimilable carbohydrate and an assimilable nitrogen source, such as a proteinaceous material. Preferred carbon sources include glucose, mannitol, levulose, sucrose, starch, ribose and the like. Preferred nitrogen sources include corn steep liquor, yeast extract, soybean meal, meat peptones, casein hydrolysate, beef extract and the like. It is advantageous to use combinations of these carbon and nitrogen sources to provide good growth and antibiotic production.

Production of Antibiotic 67-694 may be effected at most temperatures conducive to satisfactory growth of the microorganism; e.g. between 20° and 40° C., preferably 27°-35° C. Ordinarily, optimum production is obtained in 2-7 days. The pH of the medium is maintained between 6.0 and 8.5 during the fermentation, a pH of between 7 to 8 being preferred. Prior to sterilization and inoculation, the fermentation medium is usually adjusted to pH 7.0, re-adjustments being made as required during the course of the fermentation. Alternatively, the pH may be maintained at about 7.0 by the use of buffering agents such as calcium carbonate. These buffering agents generally tend to persist throughout the course of the fermentation.

When growth is carried out in large vessels and tanks, it is desirable to produce a vegetative inoculum of about 5% of the volume of the tank in a nutrient broth by inoculating the broth culture with a slant culture or a lyophilized culture of the organism. This, the germination stage of the fermentation, usually requires from about 24 to about 120 hours with about 72 to 96 hours being preferred. When an active inoculum has been obtained, it is transferred aseptically to the larger vessel or tank containing sterile medium. During the course of the germination stage and the fermentation stage which follows, the tendency of the medium to foam is controlled by the addition of a suitable anti-foaming agent, such as, Dow Corning B ®, The Dow Chemical Company, Midland, Michigan.

The medium in which the vegetative inoculum is produced may be identical to that utilized for the production of antibiotic or it may differ so long as the medium is one in which good growth of the microorganism is obtained (e.g. similar to Media A, B, or C above).

The fermentation stage usually requires from about 24 to about 100 hours. It is to be noted, however, that peak antibiotic production is often reached in less than 72 hours. The determination of peak antibiotic production is made by sampling the fermentation at various intervals and assaying the samples. When the production of antibiotic levels off, the whole broth is made alkaline, preferably to about pH 9.5 by the addition of base, such as, an alkali metal or an alkaline earth metal hydroxide, preferably sodium hydroxide. The antibiotic is extracted from the fermentation medium with a water immiscible organic solvent such as benzene, toluene, n-butanol, methylene chloride, chloroform, ethyl acetate, amyl acetate and the like, the preferred solvent being ethyl acetate. The extract is concentrated, preferably in vacuo, to about 1/50 of the volume of the fermentation medium. The biologically active material in the concentrate is then extracted into an aqueous solution of mineral acid, preferably 0.1 N sulfuric acid. In this manner Antibiotic 67-694 is partially separated from the plurality of minor components produced by the fermentation. In those cases wherein the Antibiotic 67-694 solution still contains some of the co-produced minor components, the solution may be made basic (pH 9.5) and the above-described procedure repeated. The presence of the co-produced minor components may be determined by chromatographic procedures. The aqueous acid extract of Antibiotic 67-694 obtained by the foregoing procedure is made basic (about pH 9.5) and is re-extracted with a suitable immiscible organic solvent. The extract is concentrated, preferably in vacuo, to about 1/1000 of the original fermentation volume and is precipitated into about 10 volumes of a vigorously stirred solvent mixture comprising about 6 volumes of ether and about 4 volumes of hexane. The resulting precipitate is filtered and washed sparingly with a fresh portion of the ether-hexane mixture and set aside. The filtrate containing the antibiotic activity is evaporated to a residue and the residue dissolved in a suitable non-water miscible solvent, washed several times with water and dried over a suitable drying agent, such as anhydrous sodium sulfate. After filtration, the solution is concentrated to a residue, the residue dissolved in a minimal amount of ether, the solution filtered and added to petroleum ether (bp 30°–60° C.) with stirring. A precipitate is obtained which is usually offwhite to buff colored. This precipitate is filtered, washed sparingly with petroleum ether and dried in vacuo at about 40° C. Material obtained in this manner usually has a potency of about 700 mcg/mg as determined by the following assay procedure:

The assay technique employed is a cylinder cup assay using *Bacillus subtilis* ATCC 6633 as the test organism.

The physical conditions of the assay consist of a base layer of 21 ml. and a seed layer of 4 ml. of Antibiotic Medium No. 5. A standard curve is plotted using the following concentrations of antibiotic (mcg/mg) in 0.1 M phosphate buffer (pH 8.0): 0.64, 0.8, 1.0, 1.25, and 1.56. The reference standard has been assigned a potency of 1000 mcg/mg which means that one (1) mcg of the standard in 1.0 ml. of 0.1 M phosphate buffer will give a zone of inhibition of 17.8±1.0 mm against the test organism (*B. Subtilis* ATCC 6633). The test procedure and the test medium is substantially that described for erythromycin in Assay Methods of Antibiotics, D. C. Grove and W. A. Randall, Medical Encyclopedia Inc., New York, New York (1955) pp. 96–103.

Purification may also be effected by preparing suitable derivatives such as hydrocarboncarboxylic acid esters and/or acid-addition salts, purifying the derivative and regenerating the free antibiotic.

Alternatively, Antibiotic 67-694 assaying about 700 mcg/mg may be purified by chromatographic techniques such as the following: Dissolve the antibiotic in about nine (9) parts of halogenated lower alkane containing about 1 part of an alcohol by volume (e.g. chloroform: methanol) and place atop a column containing a solid adsorbent such as silicic acid, alumina, magnesium silicate, diatomaceous earth, cellulose and the like, preferably silica gel. The column is eluted with a mixture comprising about 80% of a chlorinated lower alkane, preferably chloroform and 20% of a lower alcohol, preferably methanol. Fractions are collected and a sample of each fraction is disc tested against *Straphylococcus aureus*. Antibiotic containing fractions are chromatographed on silica gel thin-layer plates using the same solvent mixture used on the column. This chromatographic technique is also used to determine the effectiveness of the initial separation described above, (i.e. the distribution between water and an immiscible organic solvent). In general at least two plates per fraction are run. One plate is sprayed with a suitable spray such as methanol-sulfuric acid, and heated until the location of organic matter is discernible (dark spot). The second plate is used for bioautography against *Sarcina lutea* to detect the presence and location ($R_f$) of biologically active material. When chloroform-methanol (4:1 by volume) is used and the chromatogram is run for about 1 hour, Antibiotic 67-694 has an $R_f$ of about 0.75.

The fractions containing biologically active material of like mobility ($R_f$) are combined and concentrated, preferably in vacuo, to a residue. The residue is dissolved in acetone and precipitated by the addition of ether. Substantially all of the antibiotic remains in the supernatant and may be isolated by filtration or by centrifugation and by evaporating the filtrate (supernatant) to a solid residue. This method generally affords Antibiotic 67-694 assaying about 1000 mcg/mg. Alternatively, the antibiotic may be isolated by concentrating the original broth extract to a residue, chromatographing the residue and working-up the fractions by the procedure just described.

CHEMICAL AND PHYSICAL PROPERTIES OF ANTIBIOTIC 67-694

I. Chromatography

Table IV below sets forth the results obtained by chromatographing Antibiotic 67-694 in several solvent systems. The chromatography is performed on silica gel GF plates, (thickness 250 microns) which are available commercially from Analtech Inc., Wilmington, Delaware 19801, under the trade name Uniplate®.

TABLE IV

| System | Against *S. lutea* $R_f$ of Inhibition Zone |
|---|---|
| Chloroform-Methanol 17% Ammonia, 2:1:1 | 0.98 |
| Butanol-Acetic Acid-water, 3:1:1 | 0.37 |
| Chloroform-Methanol 4:1 | 0.75 |
| Chloroform-Methanol 3:2 | 0.48 |

II. Elemental Analysis

TABLE V

| | Found | Calculated |
|---|---|---|
| Carbon | 63.18 | 64.00 |
| Hydrogen | 8.86 | 8.84 |
| Nitrogen | 2.29 | 2.41 |
| Oxygen (by difference) | 25.67 | 24.75 |
| Optical Rotation $[\alpha]_D^{25}=-33.4°$ | (C = 0.3% ethanol) | |
| Empirical Formula - $C_{31}H_{51}NO_9$ | | |
| $pk_a$ 8.7 | | |
| Molecular weight (via mass spectrometry) = 581 | | |
| Neutralization equivalent 599 | | |
| Ultra-violet spectrum (methanol) $E_1\ _{cm}^{1\%} = 238\ (240\ m\mu)$ | | |
| Melting point 110°–114° C. | | |

III. Solubility

TABLE VI

| Solvent | Solubility[a] |
|---|---|
| Water | Slightly soluble |
| Methanol | Very soluble |
| Acetone | Very soluble |
| Chloroform | Very soluble |
| Benzene | Very soluble |

TABLE VI-continued

| Solvent | Solubility[a] |
|---|---|
| Ether | Sparingly soluble |

[a] According to U.S. Pharmacopea, 17th revision (1965) pg. 8

IV. Infrared Spectrum

The infrared spectrum of Antibiotic 67-694 as a mineral oil mull is shown in FIG. 1. The major peaks and bands are set forth in Table VII below. The numerical designations are in microns: the peaks attributable to mineral oil have been omitted.

TABLE VII

| | | | |
|---|---|---|---|
| 2.87 | (M) | 7.98 | (W) |
| 3.70 | (W) | 8.44 | (S) |
| 5.80 | (S) | 8.57 | (S) |
| 5.92 | (M-S) | 9.00 | (S) |
| 6.17 | (M-S) | 9.32 | (S) |
| 7.11 | (W) | 9.55 | (S) |
| 7.60 | (M) | 9.73 | (M) |
| 7.82 | (M) | 10.17 | (M-S) |
| 10.37 | (M) | 11.95 | (W) |
| 11.15 | (W-M) | 12.62 | (W) |
| 11.48 | (W) | 13.95 | (W, brd.) |
| 11.87 | (W-M) | | |

W = Weak, M = Medium, S = Strong, brd. = Broad

V. Nuclear Magnetic Resonance Spectrum

Figure 2:
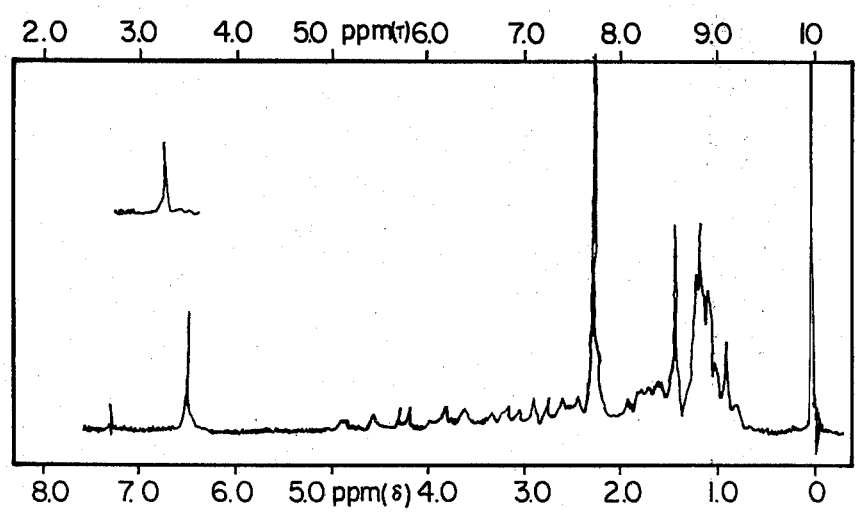

Antibiotic 67-694 has a characteristic nuclear magnetic resonance spectrum as shown by FIG. 2. The NMR spectrum was obtained by the use of a Varian A-60-A spectrometer (Varian Associates, 611 Hansen Way, Palo Alto, California). The antibiotic (40 mg.) was dissolved in about 0.4 ml. of deuterated chloroform containing a small quantity of deuterium oxide. The spectrum is recorded in parts per million (PPM) from tetramethyl silane (TMS), the internal standard. In FIG. 2, in addition to a full NMR spectrum running from 0 to 8 PPM, there is also shown a partial spectrum appearing at about 6.8 PPM. This peak normally would appear at about 9.8 PPM but would be outside the range of the spectrum normally recorded. In order to record this peak, the spectrometer was offset 180 HZ which is equivalent to about 3 PPM. In view of the intensity of the peak, it is deemed to be material to an accurate interpretation of the spectrum especially since it is indicative of the presence of an aldehyde function in the antibiotic molecule.

VII. Stability—(pH)

The activity of Antiobiotic 67-694 is not affected to a substantial degree upon being dissolved in ethanol, diluted with buffer and heated to a temperature of 100° C. for 30 minutes throughout the pH range of 2-10.

VIII. Stability to Enzymes

Antiobiotic 67-694 has been tested for stability against trypsin, chymotrypsin, pepsin, and α-amylase. Solutions of the enzymes were prepared at 1 mg./ml. in McIlvaines buffers at the optimal pH for the enzyme (i.e. trypsin and chymotrypsin pH 8; pepsin, pH 2.2; and α-amylase pH 4). Two hundred (200) mcg. of antibiotic was dissolved in 0.5 ml. of water, mixed with 0.5 ml. of enzyme solution and incubated at 37° C. for 24 hours. The solutions were disc assayed against Escherichia coli and Staphylococcus aureus after 0, 1, 2.5 and 24 hours incubation. The enzymes caused no substantial loss in activity of the antibiotic over the 24 hour interval.

IX. Color Tests

Antibiotic 67-694 gives a positive color reaction in the Molisch, Starch-KI and Elson-Morgan tests; and a negative color reaction in the biuret, ninhydrin and Sakaguchi tests.

On the basis of the foregoing physicochemical data, it is believed that Antibiotic 67-694 (rosamicin) has the following flat (planar) structure, no stereochemical assignments are being suggested by such structure:

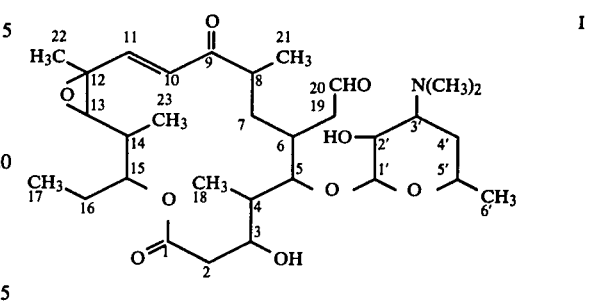

It is evident from the foregoing physiochemical data that Antibiotic 67-694 (rosamicin) is the same antibiotic designated as Juvenimicin $A_6$ in U.S. Pat. No. 3,767,793, the disclosure of which is incorporated by reference. That patent discloses the preparation of this antibiotic by culturing a Juvenimicin-producing microorganism belonging to the genus Micromonospora, e.g., *Micromonospora chalcea* var. *izumensis* (Strain No. T1124; deposited at the Institute for Fermentation, Osaka, Osaka, Japan, accession number IFO-12988, and at the American Type Culture Collection, accession number ATCC 21561).

The antibiotic isolated from the culture or that microorganism had the following properties:

(1) Elementary analysis: C: 62.97±1.0; H: 8.62±0.5; N: 3.00±0.5

(2) Specific rotation: $[\alpha]_D^{24} = 17.6°$ (c.=0.29% in $CHCl_3$)

(3) Molecular weight:
 (a) Vapour pressure osmosis method: 541±60 (in $C_6H_6$)
 (b) Titration method: 562±60
 (c) Highest mass number: m/e=581

(4) pKa: 8.4 (in 66% dimethylformamide)

(5) Color reaction:
 (a) Erythromycin test: negative
 (b) Carbomycin test: negative
 (c) Dragendorff reaction: positive (6) Solubilities:
 Soluble in benzene, chloroform, ethyl acetate, dimethylformamide, ethanol or an aqueous acid solution;
 Insoluble in petroleum ether, n-hexane or a neutral water (7) $R_f$-values on thin layer chromatography on silica gel: Eluted with mixture of chloroform, methanol and 7% aqueous ammonia solution (40:12:20): $R_f = 0.7 \pm 0.05$ (8) Ultraviolet absorption: $\lambda_{max}^{EtOH} = 240 \pm 2$ mμ ($E_{1\ cm}^{1\%} = 230 \pm 30$)

(9) Infrared absorption spectrum: The main absorption bands in wave number (cm$^{-1}$) in KBr disc are as follows: 3450, 2960, 1725, 1695, 1625, 1458, 1383, 1314, 1276, 1250, 1180, 1167, 1111, 1072, 1047, 1027, 983, 966, 932, 896, 869, 846, 834, 792, 755, 713

The following ranges of physiochemical data embraces both those disclosed for Juvenimicin $A_3$ in U.S. Pat. No. 3,767,793 and those disclosed in our prior applications Ser. Nos. 4,916 and 303,833 for Antibiotic 67-694:

(1) Elementary analysis: C: 63.00±1.0; H: 8.62±0.5; N: 3.0±0.8

(2) Specific rotation $[\alpha]_D^{24} = -17.6° \pm 18$ (C=0.29% in $CHCl_3$)

(3) Molecular weight:
(a) Vapors pressure osmosis method: 541±60 (in $C_6H_6$)
(b) Titration method: 562±60
(c) Highest mass number: m/e=581

(4) pKa: 8.4±1 (in 66% dimethylformamide)

(5) Color reaction:
Dragendorff reaction: positive (6) Solubilities:
Soluble in benzene, chloroform, ethyl acetate, dimethylformamide, ethanol or an aqueous acid solution;
Insoluble in petroleum ether, n-hexxane or a neutral water (7) $R_F$-values on thin layer chromatography on silica gel: Eluted with mixture of chloroform, methanol and 7% aqueous ammonia solution (40:12:20): $R_F=0.7\pm0.1$ (8) Ultraviolet absorption: $\lambda_{max}^{EtOH}=240\pm2$ m$\mu$ ($E_1$ $cm^{1\%}=230\pm30$)

(9) Infrared absorption spectrum: A main absorption band ($cm^{-1}$) in KBr disc appears at a point in each of the following wave number ranges: 3450-3530, 2925-60, 1724-30, 1689-95, 1620-6, 1458-60, 1380-3, 1310-14, 1275-6, 1250, 1180-7, 1165-7, 1110-1, 1070-2, 1043-9, 1025-7, 980-4, 960-6, 930-2, 895-6, 860-6, 930-2, 895-6, 868-9, 834-42, 792, 712-3 plus one at 1400-6 or 755

Antiobiotic 67-694 is capable of forming non-toxic pharmaceutically acceptable acid addition salts with inorganic and organic acids by virtue of the dimethylamino group at position 3'. By "non-toxic pharmaceutically acceptable acid addition salts" is meant those that do not exhibit toxic manifestations at normal therapeutic doses. Exemplary of such salts are those formed with such as acids as hydrochloric, sulfuric, phosphoric, citric, acetic, propion tartaric, maleic, benzoic, cyclopropylcarboxylic, adamantyl carboxylic and the like. Acid addition salts may be prepared by methods generally used in the art such as by adding a stoichiometric amount of acid to a solution of the antibiotic in a non-reactive organic solvent and isolating the salt by art known methods such as precipitation of the salt with a solvent wherein the salt is not appreciably soluble, e.g. diethyl ether. A non-reactive organic solvent is one which does not react with the antibiotic, the acid or the salt.

The hydroxyl groups at positions 3 and 2' are amenable to esterification to form non-toxic pharmaceutically acceptable esters such as, for example, those formed by reaction with typical acylating agents such as with anhydrides or chlorides or organic acids especially hydrocarbon carboxylic acids. Further, Antibiotic 67-694 is susceptible to the formation of monoesters at positions 3 and 2' and is capable of being converted into a 3,2'-diester. In general, the 2'-monoester may be prepared by selective esterification techniques generally known in the art, such as, for example treating the free antibiotic with a stoichiometric quantity (or a slight excess) of an acylating agent, such as an acyl anhydride or acyl halide at about ambient temperatures from about 1 to about 20 hours until esterification is substantially complete and isolating the 2'-monoester from the reaction mixture.

In general, 3,2'-diesters may be prepared by treating the free antibiotic with an excess of acylating agent at about ambient temperature for from about 1 to about 7 days until esterification is substantially complete and isolating the 3,2'-diester from the reaction mixture.

Alternatively, 3,2' diesters may be prepared by treating a 2'-monoester with an excess of acylating agent at about ambient temperature for from about 1 to about 7 days until esterification is complete and isolating the 3,2'-diester from the reaction mixture. The latter procedure is especially advantageous for preparing "mixed" esters (i.e. those having a different acyl group on each of positions 3 and 2').

A 3-monoester may generally be prepared by selective hydrolysis or solvolysis of a 3,2'-diester, the 2'-ester being more susceptible to hydrolytic or solvolytic removal. The preparation of 3-monoesters of rosamicin is described in application Ser. No. 303,903, filed Nov. 15, 1972, bearing the title, Novel Monoesters of Rosamicin.

It is to be noted that the 2'-monoesters, the 3,2'-diesters and the 3-monoesters of Antibiotic 67-694 all have the further property of forming acid addition salts which usually have enhanced water solubility.

BIOLOGICAL PROPERTIES OF ANTIBIOTIC 67-694

I. In Vitro Activity

The in vitro activity of Antibiotic 67-694 is ascertained by conventional tube dilution procedures using yeast beef broth medium at pH 7.4. The tubes are incubated for 18 hours at 37° C. prior to being observed. The results of a typical determination are set forth in Table IX and demonstrate that the antibiotic exhibits broad antibacterial spectrum in vitro with a greater effect upon gram-positive bacteria.

TABLE IX

| Organism | No. Strains | $MIC^A$(mcg/ml) Range |
|---|---|---|
| Staphylococcus aureus | 6 | 0.03-3.0 |
| Streptococcus pyogenes | 7 | 0.75-3.0 |
| Enterococcus sp. | 2 | .03-.03 |
| Diplococcus Pneumoniae | 3 | .03-.08 |
| Escherichia coli | 3 | 3.0 |
| Klebsiella pneumoniae | 4 | 0.3-3.0 |
| Aerobacter aerogenes | 3 | .75-7.5 |
| Proteus sp. | 3 | 0.3 |
| Pseudomonas aeruginosa | 4 | 0.75-3.0 |
| Salmonella schottmuelleri | 3 | .3-3.0 |

The antibiotic sample used in this test assayed 775 mcg/mg.
$^A$Minimal Inhibitory Concentration

II. In Vivo Activity

The protective activity and the acute toxicity of Antibiotic 67-694 is tested in male CF-1 (Carworth Farms) mice weighing approximately 20 gms. each. For protection, the antibiotic is given as a suspension or a solution in an aqueous vehicle containing 0.5% carboxy methyl cellulose (CMC) in two doses; one shortly before and one 4 hours after intraperitoneal infection with the bacteria. Infected and non-treated mice (controls) generally die within 18 hours. Survival rate in the treated group is determined 48 hours after infection.

The acute toxicity of Antibiotic 67-694 is measured in the standard manner by administering the antibiotic by a variety of routes and determining the LD$_{50}$ by standard procedures. The results of in vivo tests using a representative gram-positive and a representative gram negative organism are set forth in Tables X and Xi below:

TABLE X

| | Protective Activity of Mice | |
|---|---|---|
| Organism | Route | PD$_{50}$ (mg/kg) |
| Staphylococcus aureus gray | Subcutaneous | 50 |
| | oral | 200 |
| Streptococcus pyogenes C | Subcutaneous | 50 |
| | Oral | 200 |

III. Acute Toxicity

The acute toxicity of Antibiotic 67-694 is as follows:

TABLE XI

| Route of Administration | LD$_{50}$ (mg/kg) |
|---|---|
| Intraperitoneal | 350 |
| Subcutaneous | 625 |
| Intravenous | 155 |

Antibiotic 67-694 may be used alone or in combination with other antibacterial agents to prevent the growth of, or to reduce the number of susceptible organisms, especially the gram positive organisms set forth in Table IX above. Thus, Antibiotic 67-694 is useful in wash solutions for sanitary purposes, as in the cleaning of laboratory glassware and equipment. Further, it may be used for laundering purposes such as a bacteriostatic rinse for laboratory uniforms. Additionally, Antibiotic 67-694 may be used to treat laboratory and domestic animals that are infected with susceptible organisms.

EXAMPLE 1

Shake Flask Fermentation of *Micromonospora resaria*

1. Germination Stage:

Under aseptic conditions, inoculate a 300 ml. flask containing 100 ml. of sterile Medium A with a loopful of *M. rosaria* culture from an agar slant or add an equivalent quantity of lyophilized culture. Incubate the contents of the flask at about 35° C. for about 72 hours with agitation, preferably on a rotary shaker.

2. Fermentation Stage:

Transfer aseptically 5 ml. of inoculum from the germination stage to each of a number of 500 ml. Erlenmeyer flasks containing 100 ml. of sterile Medium B and incubate at about 28° C. for from about 72 to about 100 hours with agitation, preferably on a rotary shaker. After the first 24 hours the fermentations are sampled periodically and the sample assayed to determine when peak production is attained. When the fermentations are complete, it is usually advantageous to pool them for workup.

EXAMPLE 2

Tank Fermentation of Micromonospora Rosaria

1. Germination Stage:

Transfer aseptically 25 ml. of inoculum, (prepared as in the germination stage of Example 1), into a 2 liter Erlenmeyer flask containing 500 ml. of sterile Medium A and incubate for about 72 hours to about 28° C., preferably on a rotary shaker.

2. Fermentation Stage:

Transfer aseptically the entire 500 ml. of the second germination stage for a 14 liter fermentor containing 9.5 liters of Medium B. Add 6 ml. of antifoam (Dow-Corning B) and adjust the pH of the mixture to about 7.0 either with dilute (1.0 N) sodium hydroxide or with dilute (1.0 N) sulfuric acid as required. Ferment the mixture at about 28° C. until peak activity is attained as determined by periodic assay of the fermentation medium. This usually requires from about 72 to about 100 hours.

EXAMPLE 3

Isolation of Antibiotic 67-694

Adjust the fermentation medium prepared as in Example 2 to about pH 9.5 with 1 N sodium hydroxide and extract the medium with ethyl acetate. Combine the ethyl acetate extracts and concentrate to about 200 ml. in vacuo. Extract the concentrate containing biologically active material with about 200 ml. of 0.1 N sulfuric acid. Adjust the pH of the aqueous layer to about pH 9.5 with 1.0 N sodium hydroxide solution and re-extract with ethyl acetate. Concentrate the ethyl acetate extracts to about 10 ml. in vacuo and precipitate by pouring into about 10 volumes of a vigorously stirred solvent mixture comprising 6 volumes of ether and 4 volumes of hexane. Filter the solution, wash the precipitate sparingly with a fresh portion of the ether-hexane mixture and combine the filtrate and washings. Concentrate the filtrate to a residue; dissolve the residue in about 5 ml. of ether and filter the solution. Add the solution to about 10 volumes of petroleum ether (bp 30°-60° C.) with stirring to obtain a precipitate. Filter the off-white to buff colored precipitate and wash sparingly with petroleum ether. Dry at about 40° C. in vacuo. The material obtained in this manner usually assays about 700 mcg/mg.

EXAMPLE 4

Purification of Antibiotic 67-694

Dissolve the precipitate obtained in Example 3 in a mixture of nine parts by volume chloroform and one part methanol. Add the solution to a column containing 250 gms of silicic acid, and elute the column with a mixture of chloroform (8 parts by volume) and methanol (2 parts by volume). Collect 5 ml. fractions at the rate of about 0.5 ml./minute. Sample each fraction and disc test against *S. aureus*. Chromatograph a portion of each sample on a Uniplate ®.Ractions containing Antibiotic 67-694 will have an R$_f$ value of about 0.4 to about 0.5 Concentrate these fractions in vacuo to a residue. Dissolve the residue in acetone and add ether to form a precipitate. Remove the precipitate by filtration or by centrification and discard the precipitate. Evaporate the filtrate or supernatant to a solid residue and obtain thereby Antibiotic 67-694 assaying about 1,000 units per mg. and having the following physical constants:

M.p. 110°-114° C.

$[\alpha]_D^{25} = -33.4°$ (C=0.3% ethanol) E$_1$ $_{cm}^{1\%}$=238 (240 mµ)

EXAMPLE 5

Alternative Purification of Antibiotic 67-694

Adjust the fermentation medium prepared as in Example 2 to about pH 9.5 with one normal sodium hydroxide and extract the medium with ethyl acetate. Concentrate the ethyl acetate to a residue in vacuo. Dissolve the residue in a chloroform-methanol mixture (9 parts by volume to 1 part by volume) and add to a silicic acid column. Elute the column with a mixture of chloroform and methanol (8 parts by volume to 2 parts by volume). Collect 5 ml. fractions and sample each fraction. Disc test a portion of each sample against *S. aureus* and chromatograph a second portion of each sample on a Uniplate ®. Combine the fractions having similar $R_f$ values. Those containing Antibiotic 67-694 have an $R_f$ of about 0.4 to about 0.5. Combine these fractions, concentrate to a residue in vacuo. Dissolve the residue consisting substantially of Antibiotic 67-694 assaying about 1,000 mcg/mg having the following constants:

$[\alpha]_D^{25} = -33.4°$ (C=0.3% ethanol)
$E_{1\ cm}^{1\%} = 238$ (240 m$\mu$)

EXAMPLE 6

Antibiotic 67-694 Potassium Dihydrogen Phosphate Salt

Add 500 mg. of Antibiotic 67-694 to 13 ml. of water. Add 130 mg. of potassium dihydrogen phosphate and stir at room temperature for 2 hours. Add about 50 mg. of decolorizing charcoal and stir for an additional 15 minutes. Filter the solution and lyophilize to obtain the title product, m.p. 118°–121° $[\alpha]_D^{20} = -21.2°$ C=0.3% water.

By utilizing substantially the procedure of this example and by substituting equivalent quantities of acids having substantial solubility in water such as hydrochloric, sulfuric, phosphoric, acetic, succinic, citric, lactic, malic, malonic, maleic and the like, their respective (non-toxic) acid addition salts may be prepared. Generally, such salts exhibit in vitro and in vivo antibacterial spectra that are quite similar, if not identical, to that of the free nitrogen base. Where differences do appear, they are usually attributable to difference in solubility. For example, by virtue of their solubility in aqueous media, the foregoing salts are particularly well suited for utilization in aqueous preparations and solutions for oral and parenteral administration.

EXAMPLE 7

Antibiotic 67-694 Tartrate Salt

Dissolve 1 g. of Antibiotic 67-694 in 50 ml. of diethyl ether; add a solution of 250 mg. of tartaric acid in 1.5 ml. of ethanol. Stir the resulting mixture for about 15 minutes, then filter the precipitated salt. Wash the precipitate with diethyl ether; dry the precipitate and obtain thereby the title product, m.p. 129°–134° C., $[\alpha]_D^{20} = -12°$ (C=0.3% H$_2$O).

By utilizing substantially the procedure of this example and by substituting equivalent quantities of acids having substantial solubility in ether-alcohol mixtures such as glutaric, lauric, adamantoic, cinnamic, camphoric, palmitic, stearic, undecylenic and the like, their respective (non-toxic) acid addition salts may be prepared. Generally, due to their molecular weight and solubility characteristics, these salts are particularly well suited for utilization in topical preparations such as creams and ointments.

EXAMPLE 8

Antibiotic 67-694 2'-Acetate

Dissolve 1.0 g. of Antibiotic 67-694 in 10 ml. of dry acetone and add 0.17 ml. of acetic anhydride. Stir the mixture at room temperature for 4 hours, then slowly and with stirring add 1.2% ammonium hydroxide solution to precipitate the product. Filter the resulting precipitate, wash with dilute aqueous acetone, with water and dry. Crystallize from aqueous acetone to obtain the desired product, m.p. 112°–116° C. $[\alpha]_D^{20} = -25°$ (C=0.3% ethanol).

EXAMPLE 9

Antibiotic 67-694 2'-Isovalerate

Dissolve 2.0 g. of Antibiotic 67-694 in 10.0 ml. of dry acetone and add 0.65 ml. of isovaleric anhydride. Stir the mixture at room temperature for 16 hours, then slowly and with stirring add 1.2% ammonium hydroxide solution to precipitate the product. Filter the resulting precipitate, wash with dilute aqueous acetone, with water and dry. Crystallize from aqueous acetone to obtain the title product.

EXAMPLE 10

Antibiotic 67-694 2'-Stearate

Dissolve 3.7 g. of rosamicin in 20 ml. of acetone and add 2.5 g. of stearoyl chloride and 1.7 g. of sodium bicarbonate. Stir the mixture at room temperature for four days, then filter and concentrate the filtrate to a residue under reduced pressure. Purify the residue comprising the crude desired product by chromatography on silica gel. Elute the product with chloroform, combine fractions containing the pure product and concentrate to a residue of Antibiotic 67-694 2'-stearate, $[\alpha]_D - 16°$ (C=0.3% ethanol), $\lambda_{max}^{MeOH}$ 235 nm ($\epsilon$14,700), bioassay 585 mcg/mg.

By substituting an equivalent quantity of other acylating agents for those used in Examples 8, 9 and 10 above and by following the procedures of said Examples, other monoesters of Antibiotic 67-694 may be obtained.

EXAMPLE 11

Antibiotic 67-694 2'-Propionate

Dissolve 50.0 g. of rosamicin in 700 ml. of acetone and add 13.1 g. of propionic anhydride (1.2 m/m). Stir at room temperature for 26 hours, then evaporate the solvent under reduced pressure and triturate the residue with dilute ammonium hydroxide solution for approximately 10 minutes. Collect the residue by filtration and wash with distilled water. Re-triturate the precipitate with distilled water for approximately 10 minutes and then collect the residue by filtration and wash with distilled water. Dry the product at 45° C. and reduced pressure for 24 hours, m.p. 128°–130° C., $[\alpha]_D - 24.2$ (C=0.3% ethanol).

EXAMPLE 12

Antibiotic 67-694 3,2'-Diacetate

Dissolve 5.0 g. of Antibiotic 67-694 in 50 ml. of pyridine; add 2.5 ml. of acetic anhydride and hold the resulting solution at room temperature for about 4 days. Concentrate the pyridine solution in vacuo to a residue, keeping the temperature at about 35° C. Dissolve the residue in acetone and dilute the solution with 5% ammonium hydroxide to yield the product of this example as a suspension. Filter the suspension and wash with water. Crystallize the product from aqueous acetone to obtain the title product, m.p. 104°–107° C. $[\alpha]_D^{20} = -24°$ (C=0.3% ethanol).

EXAMPLE 13

Antibiotic 67-694 3,2'-Dibenzoate

Dissolve 250 mg. of Antibiotic 67-694 in 5 ml. of pyridine and add 0.25 ml. of benzoyl chloride with stirring. Keep the solution at room temperature for 5 days, then concentrate in vacuo to about 1 ml. and dilute with about 5 ml. of acetone. Add 5% ammonium hydroxide until the product precipitates. Filter the suspension, wash the precipitate with water and dry to obtain Antibiotic 67-694 dibenzoate.

By substituting an equivalent quantity of other acylating agents for those used in Examples 12 and 13 above and by following the procedures of said Examples, other 3,2'-diesters of Antibiotic 67-694 may be obtained. Exemplary of such esters are those derived from such acids as propionic, butyric, valeric, hexanoic, stearic, cyclopropyl carboxylic, adamantane carboxylic, pivalic, phenylacetic, phenoxyacetic, phosphoric, alkyl, aryl and aralkyl sulfonic acids, the aryl and aralkyl sulfonic acids optionally bearing substituents such as halogeno, nitro, lower alkoxy and the like on the benzenoic moiety. Also, included among such esters are hemi-esters derived from di-carboxylic acids such as succinic, maleic, fumaric, malonic and phthalic acids.

By preparing a particular monoester of Antibiotic 67-694 and by subjecting the monoester to the action of a different acylating agent, one may prepare a mixed diester such as those set forth in Examples 14 and 16, which mixed diesters are within the scope of the term "3,2'-diesters" as used herein.

Preferred non-toxic pharmaceutically acceptable 2'-monoesters and 3,2'-diesters of Antibiotic 67-694 are esters of hydrocarbon carboxylic acids of 2–18 carbon atoms, preferably alkanoic acids of 2–6 carbon atoms. Other esters, in addition to the above-identified preferred class of esters are those of inorganic acids such as, sulfuric and phosphoric acids; and of organic acids including alicyclic, cycloaliphatic, aryl and heterocyclic carboxylic, sulfonic and carbonic acids of 2–18 carbon atoms.

EXAMPLE 14

Antibiotic 67-694 3-Valerate-2'-Acetate

Stir a solution of 623 mg. of Antibiotic 67-694 2'-acetate and 0.5 ml. of valeric anhydride in 10 ml. of pyridine at room temperature for 24 hours. Concentrate to a residue under reduced pressure and triturate the residue with ammonium hydroxide. Extract the resulting mixture with ethyl acetate and wash the extracts with sodium bicarbonate and water. Concentrate the organic solution to a resiude of the desired compound, m.p. 85°–86°, mass spectrum M+ 707.

EXAMPLE 15

Antibiotic 67-694 3,2'-Dipropionate

Dissolve 1.0 g. of Antibiotic 67-694 in 12 ml. of pyridine and add 1.7 ml. of propionic anhydride. Stir the mixture at room temperature for 5 days, then concentrate to a residue under reduced pressure. Triturate the residue with 5% aqueous ammonium hydroxide and isolate the resulting solid by filtration. Purify by filtration through a column of silica gel, using chloroform as the solvent-eluent. Combine fractions containing the desired compound on the basis of thin layer chromatography, and concentrate to a solid comprising the desired dipropionate, m.p. 85°–87°, $[\alpha]_D$ −18° (ethanol) $\lambda_{max}^{MeOH}$ 240 mµ (ε14,000).

EXAMPLE 16

Antibiotic 67-694 3-Benzoate-2'-Acetate

Stir a solution of 300 mg. of Antibiotic 67-694 2'-Acetate and 0.5 ml. of benzoyl chloride in 10 ml. of pyridine at room temperature for 48 hours. Concentrate the solution to a residue under reduced pressure and triturate with ammonium hydroxide. Dissolve the solids in ethyl acetate, wash with sodium bicarbonate solution and with saturated sodium chloride and dry over sodium sulfate. Concentrate under reduced pressure to a residue of the desired compound, m.p. 76°–78°, $[\alpha]_D$ −12° (C=0.3% ethanol).

The 3-monoesters of Antibiotic 67-694 are prepared from the 3,2'-diesters substantially as set forth in Examples 17 through 20, inclusive.

EXAMPLE 17

Antibiotic 67-694 3-Valerate

Stir a solution of 625 mg. of the product of Example 14 in 20 ml. of 75% aqueous methanol at room temperature for 4 hours. Replace the solvent with ethyl acetate, wash with sodium bicarbonate and concentrate to a residue of the compound of this example, m.p. 104°–105°, $[\alpha]_D$ −39° (C=0.3% ethanol).

EXAMPLE 18

Antibiotic 67-694 3-Propionate

Dissolve 35 mg. of the product of Example 15 in 0.5 ml. of 92% aqueous methanol and allow the solution to stand at room temperature for 18 hours. Concentrate the solution under reduced pressure to give a residue comprising the compound of this example, m.p. 93°–95°.

Alternatively, dissolve 20 mg. of the product of Example 15 in a mixture of 0.5 ml. of methanol and 0.5 ml. of 5% ammonium hydroxide solution. Allow to stand at room temperature for 3 hours, then concentrate under reduced pressure to a residue consisting substantially of the compound of this example.

EXAMPLE 19

Antibiotic 67-694 3-Acetate

Dissolve 185 mg. of the product of Example 12 in 8.0 ml. of 80% aqueous methanol and keep at room temperature for 4 hours. Concentrate to a residue, dissolve the latter in chloroform, filter through 1.5 g. of silica gel and concentrate to a residue under reduced pressure. Dissolve the residue in chloroform and crystallize from chloroform-hexane to obtain the compound of this example as a chloroform solvate, m.p. 108°–110°. Recrystallize from chloroform-hexane and dry in vacuo at 60° to obtain the solvent-free compound, m.p. 145°–147°, $\lambda_{max}^{MeOH}$ 239 mµ (ε14,000).

EXAMPLE 20

Antibiotic 67-694 3-Benzoate

Keep a solution of 40 mg. of the product of Example 13 in one ml. of 80% aqueous methanol at room temperature for 40 hours. Concentrate to a residue under reduced pressure. Dissolve the residue in methanol and pour into ice water. Isolate the resulting precipitate by filtration, wash with water and dry to obtain the compound of this example, m.p. 111°–115°, mass spectrum M+ 685.

Alternatively, prepare the compound of this example in the following manner:

Stir a solution of 160 mg. of the product of Example 16 in 10 ml. of 75% aqueous methanol at room temperature for 4 hours. Replace the solvent with ethyl acetate, wash with water, dry and concentrate to obtain Antibiotic 67-694 3-benzoate identical to material prepared above.

The following examples set forth methods for preparing acid addition salts of rosamicin esters. These compounds, like the esters from which they are prepared, exhibit substantial antibacterial activity.

EXAMPLE 21

Antibiotic 67-694 2'-Propionate Phosphate Salt

Add 319 mg. of Antibiotic 67-694 2'-propionate to a solution of 49 mg. of phosphoric acid in 5 ml. of water and stir the mixture at room temperature for five minutes. Filter the solution and lyophilize the filtrate to obtain a residue of the desired phosphate salt, $[\alpha]_D -22°$ (C=0.3% water), $\lambda_{max}^{MeOH}$ 240 nm ($\epsilon$13,600), bioassay 915 mcg/mg.

EXAMPLE 22

Antibiotic 67-694 2'-Propionate Dodecylsulfate Salt

Dissolve 4.0 g. of Antibiotic 67-694 2'-propionate in 40 ml. of acetone and add a solution of 1.8 g. of sodium dodecylsulfate in 30 ml. of water. Add 0.4 ml. of acetic acid and stir the mixture for five minutes. Concentrate to about 20 ml. under reduced pressure, add about 50 ml. of water and refrigerate for 16 hours. Decant the supernatant liquid and triturate the residue with hexane. Remove the hexane by decantation, dissolve the residue in ethanol and concentrate the solution to dryness under reduced pressure, to obtain a residue of the desired salt, $\lambda_{max}^{MeOH}$ 240 nm ($\epsilon$14,000), bioassay $\pi$21 mcg/mg.

The following examples are directed to some of the plurality of dosage forms wherein Antibiotic 67-694 its non-toxic acid addition salts and esters may be employed. The formulations, excluding the topicals, are designed to permit the administration of from about 5 to about 50 mg. of antibiotic (as the free base) per kilogram of body weight per day. It is expected that the medicaments be administered up to about 8 times in a 24 hour period. The topical formulations are generally applied to the infected area from about 2 to about 4 times daily. It should be noted, however, that the size of the dosage administered and the frequency thereof depend to a great extent upon the type of infection, its severity and the individual characteristics of the animal species being treated.

| Capsule | |
|---|---|
| Antibiotic 67-694 | 250.00 mg. |
| Lactose | 248.75 mg. |
| Magnesium Stearate | 1.25 mg. |
| | 500.00 mg. |

Procedure:
1. Blend the Antibiotic 67-694 and the lactose
2. Add the magnesium stearate and mix
3. Fill capsule

EXAMPLE 24

Oral Suspension (to give a dose of 125 mg/5 ml)

| | |
|---|---|
| Antibiotic 67-694 Tartrate | 25.00 gms. |
| Magnesium aluminum silicate | 9.5 gms. |
| Sodium Carboxymethylcellulose, U.S.P. | 2.5 gms. |
| Sodium Citrate, U.S.P. | 25.0 gms. |
| Flavor | q.s. |
| Color | q.s. |
| Methylparaben, U.S.P. | 0.9 gms. |
| Propylparaben, U.S.P. | 0.2 gms. |
| Polysorbate 80, U.S.P. | 1.0 gms. |
| Sorbitol Solution, U.S.P. | 500.0 gms. |
| Water    q.s | 1000.0 ml. |

Procedure:
1. Heat 200 ml. of water to boiling, and dissolve in it one half of the parabens. Cool to about 70° C., then mix in the Polysorbate 80. Sprinkle in the silicate, stirring until a uniform smooth suspension results.
2. Heat an additional 200 ml. of water to boiling, and dissolve in it the remainder of the parabens. Disperse the CMC in this until a smooth gel results. Mix in the Sorbitol Solution. Then dissolve the sodium citrate.
3. Add the product of Step 2 to that of Step 1 slowly, with constant stirring. Cool the mixture to 25° C. Add the Antibiotic 67-694, tartrate flavor, and color mixing thoroughly. Add sufficient quantity of water to make the total volume 1000 ml.

EXAMPLE 25

Topical Cream:

| | |
|---|---|
| Antibiotic 67-694 2'-Acetate | 10 gm. |
| Stearic Acid | 200 gm. |
| Sorbitan Monostearate | 104 gm. |
| Sorbitan Monoleate | 20 gm. |
| Polyoxyethylene Sorbitan Monolaurate | 56 gm. |
| Water    q.s | 1000 ml. |

Procedure:
1. Heat the stearic acid, sorbitan monostearate, sorbitan monoleate, and polyoxyethylene sorbitan monolaurate to 65° C.
2. Heat about 90% of the water to 70° C.
3. Add the water to Step 1 and mix to form the cream base.
4. Slurry the Antibiotic 67-694 2'-acetate with about 10% of the water and pass through a colloid mill.
5. Add the milled slurry to the molten base and mix. Allow to cool.

EXAMPLE 26

Topical Ointment

| | |
|---|---|
| Antibiotic 67-694 3,2'-dibenzoate | 10 gm. |
| Petrolatum | 990 gm. |
| | 1000 gm. |

Procedure:
1. Melt the petrolatum.
2. Slurry the Antibiotic 67-694 diester with about 10% of the petrolatum and pass through a colloid mill.
3. Mix the milled slurry with the remainder of the molten petrolatum. Allow to cool.

EXAMPLE 27

Antibiotic 67-694 2'-butyrate

Dissolve 5.1 g of Antibiotic 67-694 in 70 ml. of acetone and add 1.65 ml. of butyric anhydride. Stir the reaction mixture at room temperature for 27 hours and isolate the product as described in Example 11 to obtain the compound of this Example: M.P. 106°-112° C., $[\alpha]_D^{26°} = -24.2$ (C=0.3% ethanol).

As previously indicated hereinabove, the antibiotics of this invention have in vitro and in vivo utility. And for in vivo application may be administered topically, orally or parenterally, preferably in admixture with suitable pharmaceutical excipients. Although the precise dose to be administered in any given dosage form depends upon many factors such as the stage and severity of the infection, the susceptibility of the infecting organism to the antibiotic and the individual characteristics of the mammalian species being treated, it is generally preferred that the antibiotic be administered at from about 5 mg. to about 20 mg. per kilogram of body weight per day divided into 2 to 4 equal doses. Where warranted larger or smaller doses may be administered, the precise regimen to be followed being left to the discretion of the practitioner.

We claim:

1. A compound selected from the group consisting of rosamicin and the non-toxic pharmaceutically acceptable acid addition salts thereof, said rosamicin being an organic substance having an infrared spectrum substantially as shown in FIG. 1, having a nuclear magnetic spectrum substantially as shown in FIG. 2, having an optical rotation at 25° measured by the D line of sodium of $-33.4°$ (C=0.3% ethanol), having a molecular weight of 381 as measured by mass spectrometry, having an empirical formula $C_{31}H_{51}NO_9$ having an m.p. of 110-114° C., having an ultraviolet spectrum with an $E_{1cm}^{1\%}=238$ at 240 m$\mu$, having an antibacterial spectrum substantially as shown in Table IX, and having a planar structural formula substantially as follows:

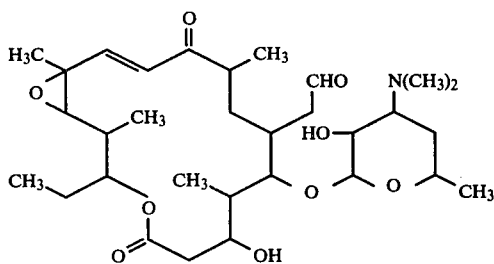

2. A compound of claim 1, rosamicin.
3. A compound of claim 1, a non-toxic pharmaceutically acceptable acid addition salt of rosamicin.
4. A compound of claim 3, rosamicin potassium dihydrogen phosphate.
5. A compound of claim 3, rosamicin tartrate.
6. A method of eliciting an antibacterial response in a mammal having a bacterial infection which comprises administering to said mammal an antibacterially effective quantity of a compound of claim 1.
7. A pharmaceutical composition comprising, in admixture with a pharmaceutically acceptable carrier, an antibacterially effective amount per unit dosage of a compound of claim 1.
8. A compound selected from the group consisting of the non-toxic pharmaceutically acceptable 2'-monoesters and 3,2'-diesters of rosamicin, and their non-toxic pharmaceutically acceptable acid addition salts, wherein each of said esters is an ester of an mono-carboxylic acid or a hemi-ester of a dicarboxylic acid, each of 2 to 18 carbon atoms, said rosamicin being an organic substance having an infrared spectrum substantially as shown in FIG. 1, having a nuclear magnetic spectrum substantially as shown in FIG. 2, having an optical rotation of 25° measured by the D line of sodium of $-33.4°$ (C=0.3% ethanol), having a molecular weight of 581 as measured by mass spectrometry, having an empirical formula $C_{31}H_{51}NO_9$ having a m.p. of 110°-114° C., having an ultra-violet spectrum with an $E_{1cm}^{1\%}=238$ at 240 m$\mu$, having an antibacterial spectrum substantially as shown in Table IX, and having a planar structural formula substantially as follows:

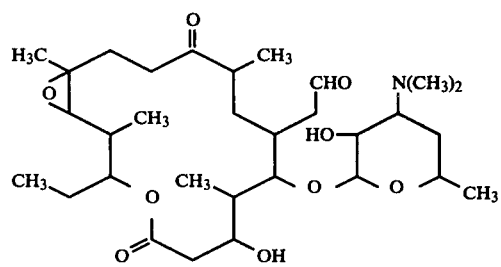

9. A compound of claim 8, a non-toxic pharmaceutically acceptable 2'-monoester of rosamicin.
10. A compound of claim 9, rosamicin 2'-acetate.
11. A compound of claim 9, rosamicin 2'-isovalerate.
12. A compound of claim 9, rosamicin 2'-propionate.
13. A compound of claim 8, a non-toxic pharmaceutically acceptable 3,2'-diester of rosamicin.
14. A compound of claim 13, rosamicin 3,2'-diacetate.
15. A compound of claim 13, rosamicin 3,2'-dibenzoate.
16. A compound of claim 13, rosamicin 3,2'-dipropionate.
17. A compound of claim 13, rosamicin 3-valerate-2'-acetate.
18. A compound of claim 13, rosamicin 3-benzoate-2'-acetate.
19. A compound of claim 8, a non-toxic pharmaceutically acceptable acid addition salt of 2'-monoester or a 3,2'-diester of rosamicin.
20. A method of eliciting an antibacterial response in a mammal having a bacterial infection which comprises administering to said mammal having said infection an antibacterially effective quantity of a compound of claim 8.
21. A pharmaceutical composition comprising, in admixture with a pharmaceutically acceptable carrier, an antibacterially effective amount per unit dosage of a compound of claim 8.

* * * * *